(12) United States Patent
Wahl et al.

(10) Patent No.: US 12,721,720 B1
(45) Date of Patent: Sep. 1, 2026

(54) IMPLANT FOR REINFORCEMENT OF SOFT TISSUES

(71) Applicant: TM HOLDING COMPANIES, INC., Cordova, TN (US)

(72) Inventors: Rebecca H. Wahl, Cordova, TN (US); Alan G. Taylor, Cordova, TN (US)

(73) Assignee: TM HOLDING COMPANIES, INC., Cordova, TN (US)

( * ) Notice: Subject to any disclaimer, the term of this patent is extended or adjusted under 35 U.S.C. 154(b) by 0 days.

(21) Appl. No.: 19/231,759

(22) Filed: Jun. 9, 2025

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/0409* (2013.01); *A61B 2017/0414* (2013.01); *A61B 2017/0441* (2013.01); *A61B 2017/0445* (2013.01); *A61B 2017/0464* (2013.01); *A61F 2002/0817* (2013.01); *A61F 2002/0841* (2013.01); *A61F 2002/0852* (2013.01); *A61F 2002/087* (2013.01); *A61F 2002/0876* (2013.01)

(58) Field of Classification Search
CPC ........ A61B 17/0401; A61B 2017/0409; A61B 2017/0414; A61B 2017/0441; A61B 2017/0445; A61B 2017/0464; A61F 2/0811; A61F 2002/0817; A61F 2002/0841; A61F 2002/0852; A61F 2002/087; A61F 2002/0876
See application file for complete search history.

(56) References Cited

U.S. PATENT DOCUMENTS

| | | | |
|---|---|---|---|
| 5,224,946 A | 7/1993 | Hayhurst et al. | |
| 5,922,026 A | 7/1999 | Chin | |
| 6,808,486 B1 | 10/2004 | O'Donnell | |
| 10,159,579 B1 * | 12/2018 | Reitblat ............ | A61B 17/7082 |
| 10,595,983 B1 | 3/2020 | Ferguson et al. | |
| 2004/0054253 A1 | 3/2004 | Snitkin et al. | |
| 2005/0192631 A1 | 9/2005 | Grafton | |
| 2007/0043255 A1 | 2/2007 | O'Donnell | |
| 2008/0004659 A1 | 1/2008 | Burkhart et al. | |
| 2009/0149700 A1 | 6/2009 | Garcia et al. | |
| 2009/0171143 A1 | 7/2009 | Chu et al. | |
| 2009/0312794 A1 | 12/2009 | Nason et al. | |
| 2010/0160962 A1 | 6/2010 | Dreyfuss et al. | |
| 2011/0009960 A1 | 1/2011 | Altman et al. | |
| 2011/0015675 A1 | 1/2011 | Howard et al. | |
| 2011/0264138 A1 | 10/2011 | Avelar et al. | |
| 2012/0078298 A1 | 3/2012 | Sklar | |

(Continued)

*Primary Examiner* — Sameh R Boles
(74) *Attorney, Agent, or Firm* — INNOVATION CAPITAL LAW GROUP, LLP; Vic Lin

(57) ABSTRACT

An implant and instrument system includes a woven implant supplied with anchors and instruments to implant it. The knotless anchor design is an interference screw-style anchor body with a rotatable eyelet offered in various sizes with a single-use instruments in sterile-packed kits. The kits are intended to facilitate repairing soft tissue, such as damaged ligaments and tendons in, for example, the foot and ankle. Each sterile kit includes an implant loaded onto a driver accompanied by an eyelet and anchor, guide wires, a tissue protector, a cannulated drill, an extra eyelet and anchors. Taps are available in separate packaging for denser/harder bone.

19 Claims, 14 Drawing Sheets

(56) References Cited

U.S. PATENT DOCUMENTS

| | | | | |
|---|---|---|---|---|
| 2012/0123473 | A1 | 5/2012 | Hernandez | |
| 2012/0130422 | A1 | 5/2012 | Hootstein | |
| 2013/0023928 | A1 | 1/2013 | Dreyfuss | |
| 2013/0035721 | A1 | 2/2013 | Brunelle | |
| 2013/0096677 | A1 | 4/2013 | Myers et al. | |
| 2013/0158596 | A1 | 6/2013 | Miller et al. | |
| 2013/0158599 | A1 | 6/2013 | Hester et al. | |
| 2013/0281770 | A1 | 10/2013 | Alinsod et al. | |
| 2014/0046380 | A1 | 2/2014 | Asfora | |
| 2014/0052179 | A1 | 2/2014 | Dreyfuss et al. | |
| 2014/0243892 | A1 | 8/2014 | Choinski | |
| 2014/0364862 | A1 | 12/2014 | Bennett et al. | |
| 2015/0066079 | A1 | 3/2015 | Schmieding | |
| 2015/0216646 | A1 | 8/2015 | Zoll et al. | |
| 2016/0113643 | A1* | 4/2016 | Diduch | A61F 2/0811 606/232 |
| 2016/0228188 | A1 | 8/2016 | Sweeney | |
| 2016/0310129 | A1 | 10/2016 | Hoeppner et al. | |
| 2016/0324552 | A1* | 11/2016 | Baker | A61B 17/1728 |
| 2017/0172562 | A1 | 6/2017 | Lombardo | |
| 2018/0235746 | A1* | 8/2018 | Pilgeram | A61B 17/0401 |
| 2019/0365366 | A1 | 12/2019 | Petry et al. | |
| 2020/0155140 | A1 | 5/2020 | Palese | |
| 2020/0170782 | A1* | 6/2020 | Smith | A61B 17/0401 |
| 2020/0360008 | A1* | 11/2020 | Breslich | A61B 17/1615 |
| 2021/0244424 | A1 | 8/2021 | Suchomel et al. | |
| 2023/0346364 | A1 | 11/2023 | Clark et al. | |
| 2024/0081807 | A1 | 3/2024 | Stone et al. | |
| 2024/0164770 | A1 | 5/2024 | Chao et al. | |
| 2024/0407777 | A1* | 12/2024 | Zeevi | A61B 17/0401 |
| 2025/0040921 | A1* | 2/2025 | Ninh | A61B 17/0485 |

* cited by examiner 32
12

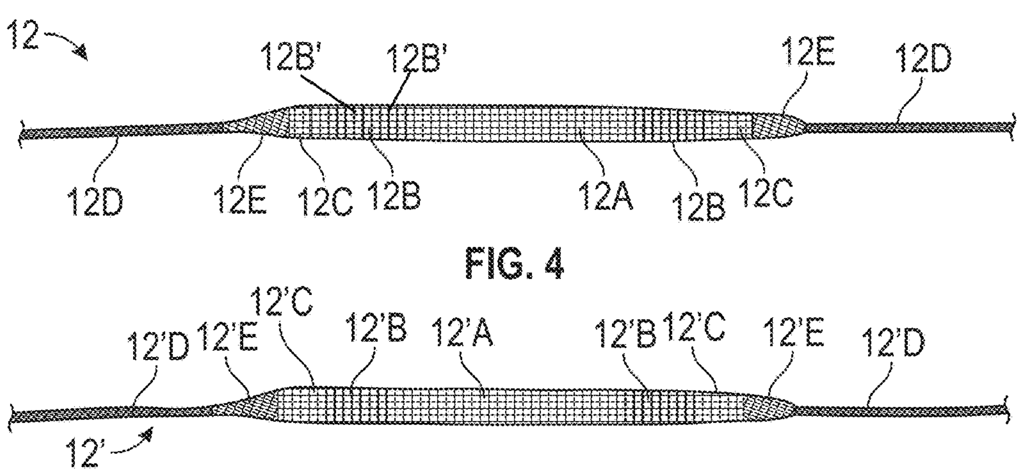
FIG. 4
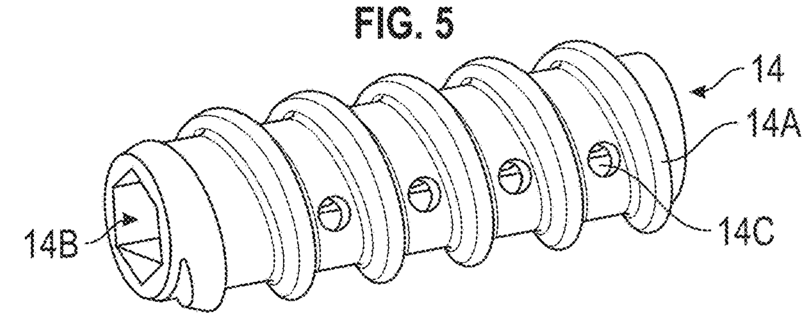
FIG. 5
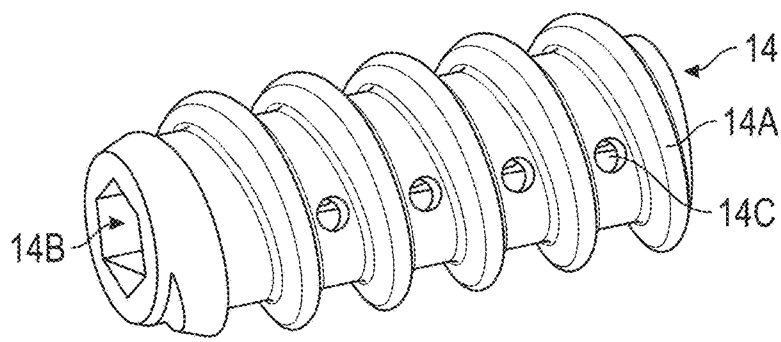
FIG. 6A
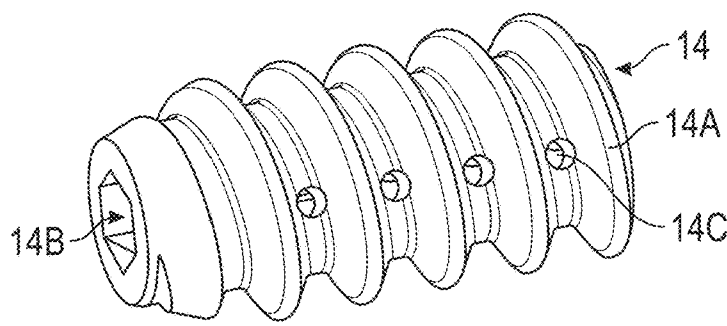
FIG. 6B
FIG. 6C 18A
16A
18B
16
16B 20A
16C
16

50
52
44
40
42
14
16

IMPLANT FOR REINFORCEMENT OF SOFT TISSUES

BACKGROUND OF THE INVENTION

1. Field of the Invention

Embodiments of the invention relate generally to medical devices and methods for using the same. More particularly, embodiments of the invention relate to an implant for the reinforcement and augmentation of soft tissues.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Soft tissue reinforcement focuses on medical grafts that are designed to support and regenerate soft tissue under or near suture lines. Soft tissue is defined as areas of similarly specialized cells that function to connect, support and surround other structures and organs of the body. These tissues include skin, subcutaneous tissue, fascia, ligaments, tendons, fibrous tissues, fat, synovial membranes and muscle.

There is a need for improved devices and methods for the augmentation and reinforcement of soft tissues.

SUMMARY OF THE INVENTION

Embodiments of the present invention provide a tissue reinforcement implant that is intended for reinforcement of soft tissues that are repaired by suture or other fixation devices during tendon and ligament repair surgery, including reinforcement of rotator cuff, patellar, Achilles, biceps, quadriceps tendon, medial collateral ligament, lateral collateral ligament, spring ligament, deltoid ligament, ulnar collateral ligament or other tendons or extra-articular ligaments. Embodiments of the present invention further provide devices and methods for performing tissue reinforcement.

Embodiments of the present invention provide an implant comprising a central portion of suture tape material that has been woven with a pore size from 100 μm to 1 mm. The central portion is hollow or tubular. Openings (i.e., pockets) have been formed on each end of a length of the central portion; and a taper to reduce a width of the implant to form cords at each end of the implant.

In some embodiments, the implant further comprises a second suture material portion within the central portion.

In some embodiments, which may be combined with the above embodiment, the central portion is tubular or hollow. In some embodiments there is no tube.

In some embodiments, which may be combined with any of the above embodiments, the central portion has a flat width from 2 mm to 20 mm.

In some embodiments, which may be combined with any of the above embodiments, the implant includes pockets for placement of biological material within the implant.

In some embodiments a different colored thread is added to the pocket areas to indicate their location.

In some embodiments, a different colored thread is woven in vertical lines across the central section to indicate measurement marks.

In some embodiments, which may be combined with any of the above embodiments, the implant is treated with a gas plasma to impart hydrophilicity to the implant.

In some embodiments, which may be combined with any of the above embodiments, the implant exhibits an elongation of from about 3 percent to about 50 percent of its overall length under load.

In some embodiments, which may be combined with any of the above embodiments, the implant is formed from a non-absorbable suture tape.

In some embodiments, which may be combined with any of the above embodiments, the implant is formed from polyester.

In some embodiments, which may be combined with any of the above embodiments, the central portion has a length from 50 mm to 600 mm.

In some embodiments, which may be combined with any of the above embodiments, the pockets each have a length from 10 mm to 50 mm.

In some embodiments, which may be combined with any of the above embodiments, the implant has an over length from 100 mm to 2000 mm.

Embodiments of the present invention provide a soft tissue augmentation device, comprising a driver having a shaft extending therefrom; an eyelet removably positioned at the end of the shaft; an anchor, rotatable by the driver, positioned on the shaft, adjacent the eyelet; and an implant configured to thread through the eyelet, the implant having ends operable to removably attach to a handle of the driver.

In some embodiments, the shaft of the driver includes an outer sleeve; an inner shaft movable within an interior of the outer sleeve; and a window formed in the outer sleeve adjacent the handle.

In some embodiments, which may be combined with the above embodiments, the device further comprises an outer sleeve line disposed on the outer sleeve at a central region of the window; and an inner shaft line disposed on the inner shaft, wherein the anchor is movable between an initial position and a fully inserted position, wherein, at the fully inserted position, the inner shaft line is visible in the window and aligns with the outer sleeve line.

In some embodiments, which may be combined with any of the above embodiments, the handle includes a front handle and a back handle, the back handle rotatable relative to the front handle.

In some embodiments, which may be combined with any of the above embodiments, the device further comprises double looped cleat slots operable to secure the ends of the implant thereto.

In some embodiments, which may be combined with any of the above embodiments, the device further comprises a guide wire; and a cannulated drill, wherein the guide wire is configured to be positioned at a location and angle for drilling into bone; and the cannulated drill fits about the guide wire to position the drill at the proper position and angle for drilling into the bone.

In some embodiments, which may be combined with any of the above embodiments, the device further comprises a tissue protector, wherein the drill passes through the tissue protector; and the drill includes a boss that contacts the tissue protector when the drill drills a hole at a predetermined desired depth.

In some embodiments, which may be combined with any of the above embodiments, the eyelet includes a slit with an increased diameter portion, the slit operable to receive an end of the shaft of the driver, the slit operable to permit removal of the eyelet from the shaft of the driver.

In some embodiments, which may be combined with any of the above embodiments, the anchor has a helical thread.

In some embodiments, which may be combined with any of the above embodiments, the anchor has a hex drive feature operable to engage with a hexagonal shaped end of the shaft of the driver.

In some embodiments, which may be combined with any of the above embodiments, the anchor includes one or more slots formed therein for increasing a surface area of the anchor.

In some embodiments, which may be combined with any of the above embodiments, the device further comprises a tap, the tap configured to tap a hole for positioning the anchor therein.

In some embodiments, which may be combined with any of the above embodiments, the implant includes a tubular central portion of suture tape material having a pore size from 100 μm to 1 mm pockets formed on each end of a length of the central portion; a second suture material portion at ends of the pockets; and a taper disposed at ends of the second suture material portion, the taper operable to reduce a width of the implant to form cords at each end of the implant.

Embodiments of the present invention provide a method for reinforcement of soft tissues comprising accessing a location at bone of a patient for placement of a reinforcement implant thereto; drilling a hole into the bone at the location; positioning a pre-loaded tissue reinforcement device at the hole, the tissue reinforcement device comprising a driver having a shaft extending therefrom, an eyelet removably positioned at the end of the shaft, an anchor, rotatable by the driver, positioned on the shaft, adjacent the eyelet, and an implant threaded through the eyelet, the implant having ends removably attached to a handle of the driver; pressing the eyelet into the hole to contact the anchor with the hole; turning the anchor to cause helical threads of the anchor to engage with the hole; monitoring a window, formed in an outer sleeve of the shaft of the driver, to determine when the anchor is fully positioned into the hole; detaching the eyelet from the driver once the anchor is fully positioned in the hole; drill a second hole at a point for fixation of the implant; placing a second anchor and a second eyelet on the shaft of the driver; threading the implant through the second eyelet; and threading the second anchor into the second hole with the implant spanning between the hole and the second hole with a desired tension.

In some embodiments, the soft tissues are repaired suture or other fixation devices.

In some embodiments, which can be combined with the above embodiments, the soft tissues are repaired during tendon or ligament repair surgery.

In some embodiments, that can be combined with any of the above embodiments, the method further comprises positioning a guide wire on the bone at the location at a desired angle; and using a cannulated drill, fit over the guide wire, for drilling the hole.

In some embodiments, that can be combined with any of the above embodiments, the method further comprises passing the drill passes through a tissue protector, wherein the drill includes a boss that contacts the tissue protector when the drill drills a hole at a predetermined desired depth.

In some embodiments, that can be combined with any of the above embodiments, the shaft of the driver includes the outer sleeve; an inner shaft is movable within an interior of the outer sleeve; and the window is formed in the outer sleeve adjacent the handle.

In some embodiments, that can be combined with any of the above embodiments, an outer sleeve line is disposed on the outer sleeve at a central region of the window; an inner shaft line is disposed on the inner shaft; and the anchor is movable between an initial position and a fully inserted position, wherein, at the fully inserted position, the inner shaft line is visible in the window and aligns with the outer sleeve line.

In some embodiments, that can be combined with any of the above embodiments, the handle includes a front handle and a back handle, the back handle rotatable relative to the front handle.

In some embodiments, that can be combined with any of the above embodiments, the implant are attached to double looped cleat slots formed in the front handle.

In some embodiments, that can be combined with any of the above embodiments, the method further comprises pulling a desired tension on the implant before securing the second anchor in the second hole; marking the implant on the shaft where an end of the second anchor would be positioned when fully inserted; aligning a center of the second anchor with the mark; and inserting the second anchor into the second hole.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

FIG. 4 illustrates a top, elongated view of the implant of FIG. 3, according to a first size thereof;

FIG. 5 illustrates a top, elongated view of the implant of FIG. 3, according to a second size thereof;

FIGS. 6A through 6C illustrate perspective views of an anchor of the tissue reinforcement system of FIG. 1, according to various sizes thereof;

Figure 1:
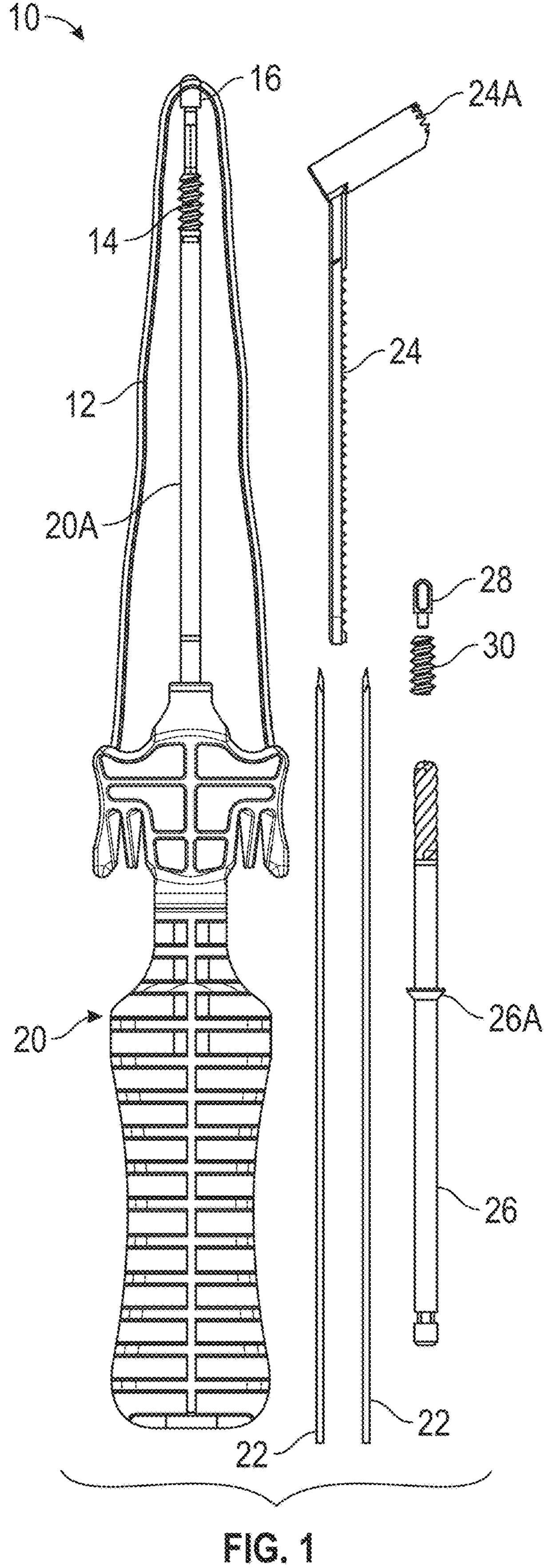
FIG. 1 illustrates a side view of a tissue reinforcement system, typically packaged as a kit for performing tissue reinforcement, according to an exemplary embodiment of the present invention.

The illustrations in the figures may not necessarily be drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

As is well known to those skilled in the art, many careful considerations and compromises typically must be made when designing for the optimal configuration of a commercial implementation of any system, and in particular, the embodiments of the present invention. A commercial implementation in accordance with the spirit and teachings of the present invention may be configured according to the needs of the particular application, whereby any aspect(s), feature (s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide an implant and instrument system that includes a woven implant supplied with anchors and instruments to implant it. The knotless anchor design is an interference screw-style anchor body with a rotatable eyelet offered in various sizes with a single-use instruments in sterile-packed kits. The kits are intended to facilitate repairing soft tissue, such as damaged ligaments and tendons in, for example, the foot and ankle. Each sterile kit includes an implant loaded onto a driver accompanied by an eyelet and anchor, guide wires, a tissue protector, a cannulated drill, an extra eyelet and anchors. Taps are available in separate packaging for denser/harder bone.

Referring to FIG. 1, a tissue reinforcement system 10, also referred to as system 10, can include a woven implant 12 supplied with anchors and instruments to implant it. The knotless anchor design is an interference screw-style anchor body 14 with a rotatable eyelet 16 offered in different sizes. For example, the anchor 14 may be provided as a 3.90 mm anchor, a 4.75 mm anchor and a 5.50 mm anchor. The anchor size may depend on the particular application and/or type and/or size of bone into which the anchor is to be secured. A kit (the system 10) can be packaged to include the components required for providing tissue reinforcement, as described in greater detail below.

The kits can be used to facilitate repairing damaged soft tissue, such as ligaments and tendons in, for example the foot and ankle. Each sterile kit includes the implant 12, typically pre-loaded onto a driver 20 accompanied by the 16 eyelet and anchor 14, two guide wires 22, a tissue protector 24, a cannulated drill 26, an extra eyelet 28 and extra or various sized anchors 30. While the guide wires 22 and the tissue protector 24 are provided in the kit and as discussed below, are recommended for use of the system 10, the specific use of one or more components, such as the guide wires 22 and the tissue protector 24, may be optional, depending on the particular application.

Figures 2, 3:
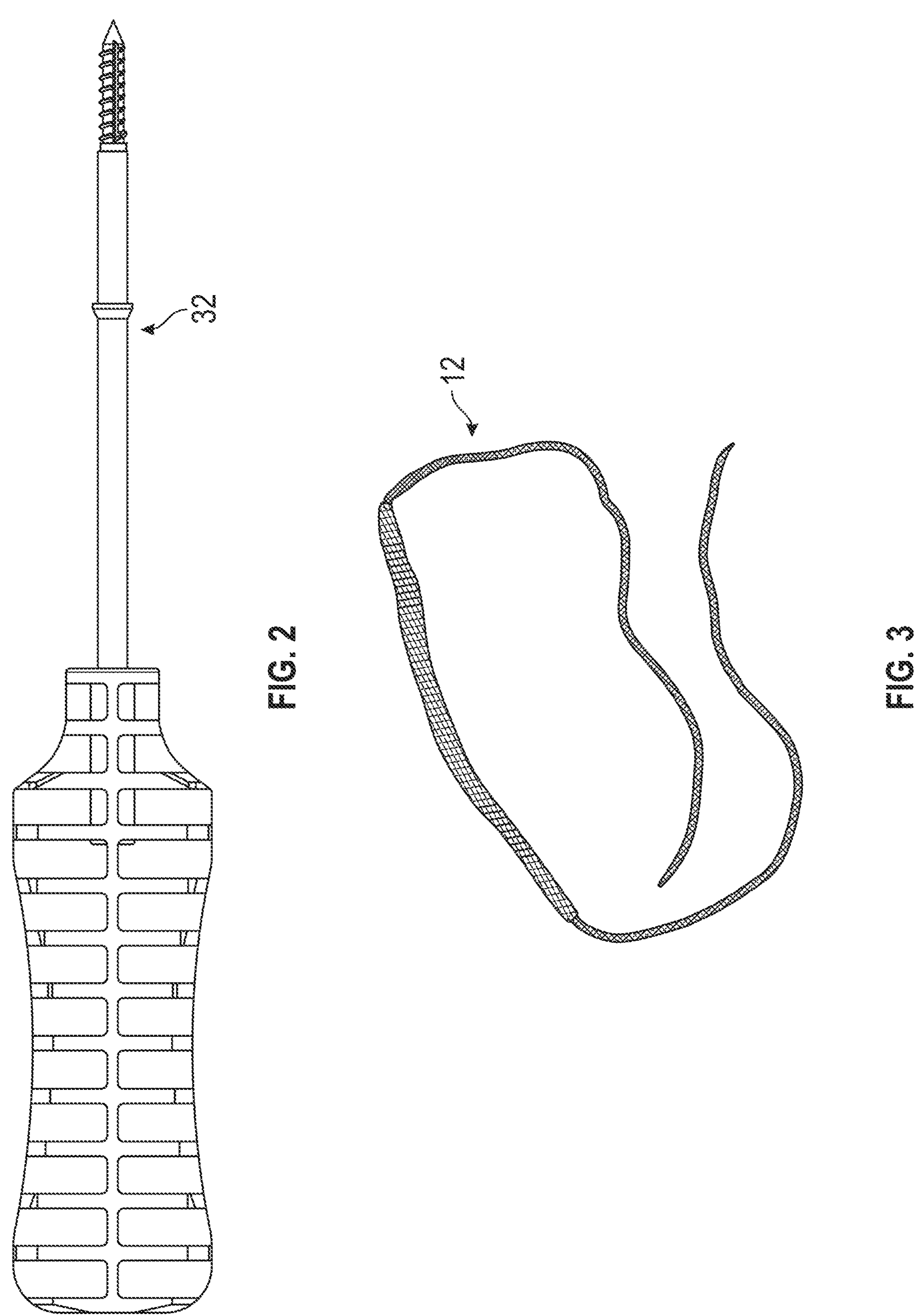
FIG. 2 illustrates side view of a tap usable with the tissue reinforcement system of FIG. 1.
FIG. 3 illustrates a perspective view of an implant of the tissue reinforcement system of FIG. 1.

Referring to FIG. 2, in some embodiments, a tap 32 may be used for tapping denser/harder bone, making it easier to place the anchor 14 into the bone (not shown).

Referring to FIGS. 2 through 4, the tissue reinforcement implant 12 can be used for reinforcement of soft tissues that are repaired by suture or other fixation devices during tendon and ligament repair surgery, including reinforcement of rotator cuff, patellar, Achilles, biceps, quadriceps tendon, medial collateral ligament, lateral collateral ligament, spring ligament, deltoid ligament, ulnar collateral ligament or other tendons or extra-articular ligaments. The implant 12 is a sterile non-absorbable implantable tape made from, for example, polyester. polyethylene, nylon, polyamide, polypropylene or a combination thereof.

The implant 12 can be treated with a gas plasma or equivalent to render the mesh hydrophilic, which serves to accelerate cell recruitment and adhesion. A hydrophilic coating using plasma treatment may be performed using oxygen plasma, for example. When exposed to a plasma of oxygen, the surface of a material can become more hydrophilic by forming polar hydroxyl groups on the surface, which readily attract water molecules.

The implant 12 can exhibit approximately 3-5% elongation under load. In other embodiments, there is a 5-25% elongation. This is similar to actual anatomical ligament and tendon elongation. Thus, when the implant 12 is used for soft tissue reinforcement of a ligament and/or a tendon, the implant 12 can illustrate elongation that mimics the soft tissue for which it is reinforcing (in this case, the ligament or tendon). In other embodiments, the implant 12 can illustrate differing degrees of elongation under load, depending on the specific application thereof.

Referring to FIGS. 4 and 5, a central portion 12A of the implant 12 can be formed as a hollow or tubular design that has pore sizes ranging from 10 microns to 1 mm to encourage tissue incorporation. The central portion 12A may be a hollow or tubular portion having a diameter from about 2 mm to about 20 mm, for example. In some embodiments, all or a portion of the central portion 12A may be formed from flat, non-tubular material.

Adjacent to the central portion 12A are two openings or pockets 12B in which a biological material can be inserted. The biological material can include, as non-limiting examples, platelet-rich plasma (PRP), allographs, autograph tendon or ligaments, amnio, xenogeneic collagen, or the like. The pockets 12B may be formed from stitching suture tape together with an opening to permit insertion into the implant 12 via the pockets 12B. In some embodiments, a thread 12B' having a color different from the remainder of the implant 12 may be used to identify the location of the pockets 12B. Typically, the pockets 12B are formed integrally with the weaving process of the implant 12. The material placed into the pockets 12B may be positioned in the central portion 12A, for example.

In the area of the pockets 12B, distal the central portion 12A, a second suture material 12C is woven into the implant 12. This facilitates pocket location. This second suture material 12C may be formed completely hollow, partially hollow, or completely as a flat member. The material placed into the pockets 12B may also be positioned at the area of the second suture material 12C. The implant 12 tapers down into circular cords 12D. The cords 12D can function to tether the implant 12 to the driver and to also facilitate threading through the anchor eyelet. In some embodiments, the second suture material 12C may be the same material as the central portion 12A. In other embodiments, the second suture material 12C may be different from the central portion 12A. Such differences may be in the type of material used, the pore size, or the like.

It should be understood that the implant 12 can be formed in various lengths depending on the particular application. The central portion 12A may be from about 50 mm to about 200 mm in length. The pockets 12B may be from about 10 mm to about 50 mm in length.

In certain embodiments, a 120 mm version of the implant 12 can include a 60 mm central portion 12A, 20 mm long pockets 12B, 10 mm second suture portions 12C, a 10 mm taper 12E to the cords 12D, which themselves may be about 280 mm in length. In another embodiment, a 250 mm version of the implant 12' can include a 160 mm central portion 12'A, 35 mm long pockets 12'B, 10 mm second suture portions 12'C, a 10 mm taper 12'E to the cords 12'D, which themselves may be about 215 mm in length. As used herein, each "version" refers to the length of the implant, not including the taper 12E, 12'E or the cords 12D, 12'D. The overall length of the implant 12, 12' may be from about 500 mm to about 1000 mm, typically about 700 mm.

Referring now to FIGS. 6A through 6C, in some embodiments, the anchor 14 can be composed of polyether ether ketone (PEEK), metals such as titanium, bioresorbable materials, such as polyglycolide (PGA) and poly-L-lactic acid (PLLA), bio-composite materials with beta-tricalcium phosphate added to the bioresorbable materials, or the like The anchor 14 can have a helical external thread 14A for rotation implantation. The anchor 14 can be cannulated with a hex drive feature, or bore, 14B formed therethrough for interconnection to the driver. This allows the anchor 14 to be positioned and move along the driver shaft 20A as the anchor is threaded into a drilled hole, as discussed in greater detail with respect to FIGS. 14A and 14B.

In some embodiments, transverse slots 14C can be formed in the anchor 14 to increase the surface area for tissue integration. The transverse slots 14C may be formed in various shapes, such as circular, elongated, squared, or any geometric or non-geometric shape. In some embodiments, the transverse slots 14C can be formed between each thread 14A of the anchor 14. In other embodiments, the transverse slots 14C may be formed between only one or more of the threads 14A. In other embodiments, transverse slots 14C may be formed through only one side of the anchor 14, thus providing fluid communication between the outside of the anchor 14 and the inside of the hex drive feature 14B formed inside the anchor 14. In other embodiments, the transverse slots 14C may be formed in a row, as shown in FIGS. 6A through 6C, or may be formed offset each other along a longitudinal axis of the anchor 14.

The anchor 14 can be provided in various sizes, depending on the particular application. The anchor 14 may be provided in diameters of, for example, 3.90 mm, 4.75 mm and 5.50 mm. The different diameter anchors may have the same length or may have different lengths. Typically, the length of the anchor 14 may range from about 8 mm to about 20 mm. In some embodiments, the anchors 14 may vary not only in length and/or diameter but also in thread height, thread pitch, thread depth, flank angle, taper angle and the like.

Figures 7, 8, 9:
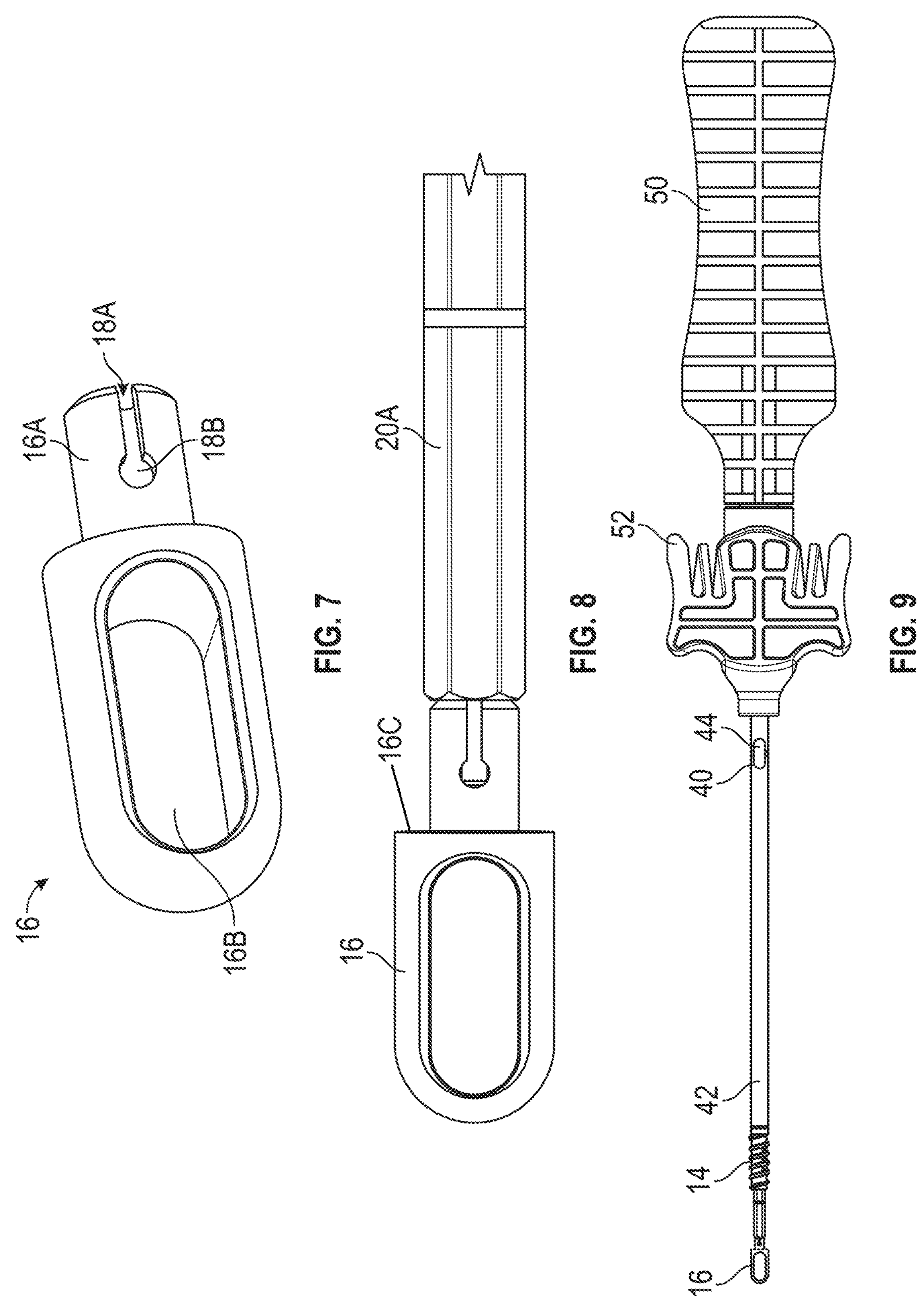
FIG. 7 illustrates a detailed perspective view of an eyelet of the tissue reinforcement system of FIG. 1.
FIG. 8 illustrates a side view of the eyelet of FIG. 7 attached onto the driver of the tissue reinforcement system of FIG. 1.
FIG. 9 illustrates a side view of a driver of the tissue reinforcement system of FIG. 1, with the implant removed therefrom for clarity, in an unthreaded or initial state.

Referring to FIGS. 7 and 8, in some embodiments, the eyelet 16 can be composed of PEEK. The eyelet 16 can have a relatively large opening 16B to accommodate easy passage of the implant 12. In a preferred embodiment, the opening has a length in a preferred range of 2 mm to 10 mm, and a width in a preferred range of 2 mm to 8 mm.

Figures 10, 11:
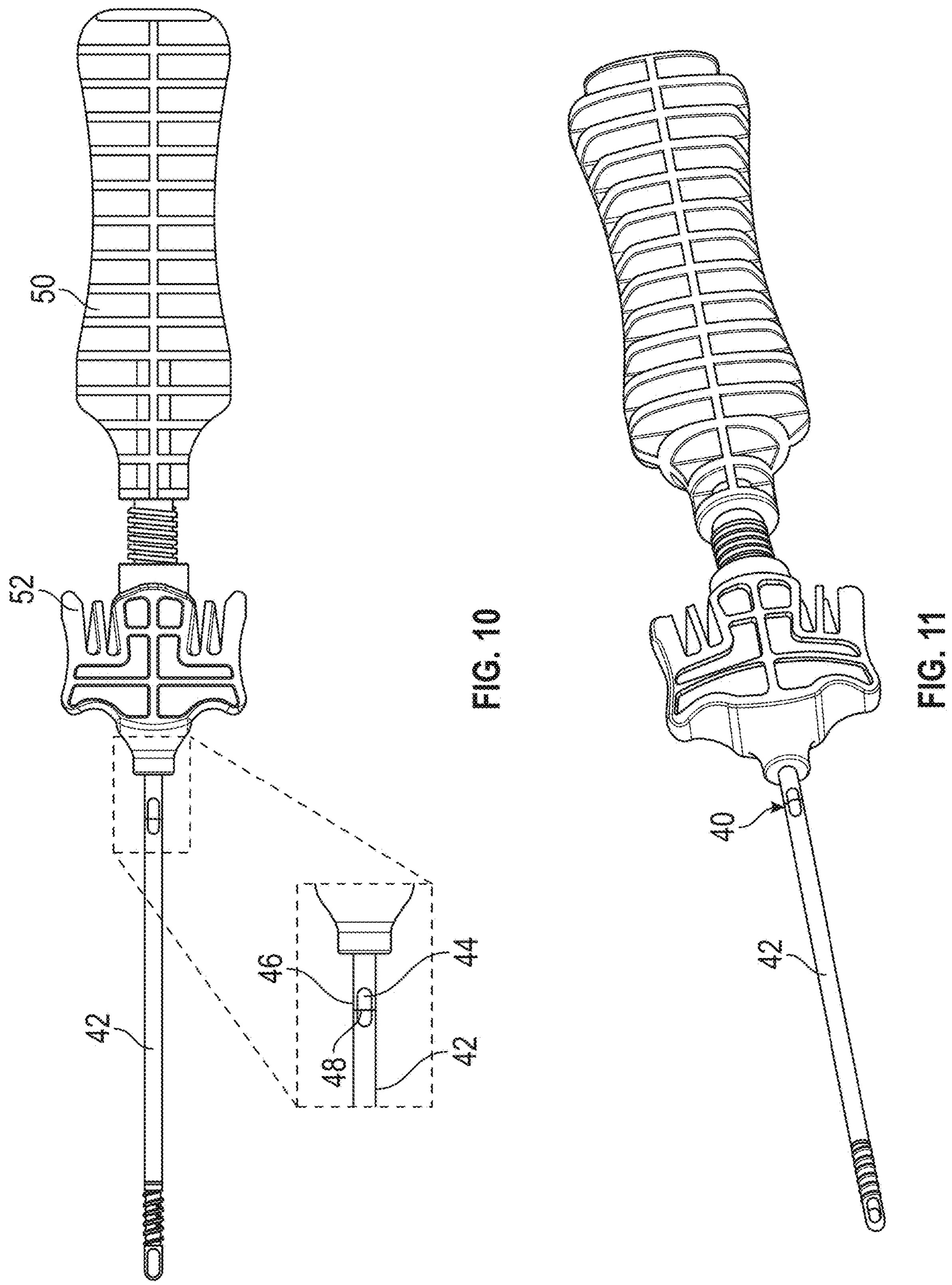
FIG. 10 illustrates a side view of the driver of FIG. 9 in a fully inserted state.
FIG. 11 illustrates a perspective view of the driver of FIG. 10.

On the shaft 16A of the eyelet 16, a feature can be provided for facilitating a repeatable interference fit with the driver shaft 20A. For example, a slit 18A with an expanded diameter interior portion 18B may be provided for releasably attaching the driver shaft 20A to the eyelet 16. This feature allows an interference fit interaction between the end of the driver shaft 20A and the eyelet 16. This interference fit then allows the eyelet 16 to stay on the driver 20 during insertion and then easily, but firmly, detach upon full implantation of the anchor 14 by simply pulling on the driver 20. The slit 18A can be formed on the shaft 16A (also referred to as the mounting end 16A), which can be formed as a hollow tubular member. The mounting end 16A has a first width. The anchor 14 can have an inside diameter larger than the first width of the mounting end 16A of the eyelet 16 to permit the mounting end 16A to fit inside the anchor 14 as illustrated in FIGS. 10 and 11, for example The eyelet 16 has a lip 16C at a distal end of the mounting end 16A, the lip 16C provides a second diameter of the eyelet 16, where the second diameter is greater than the inside diameter of the anchor 14 to prevent the eyelet 16 from moving through the anchor 14.

Referring now to FIGS. 8 through 11, a laser line window 40 can be formed in an outer sleeve 42 of the driver 20, permitting visualization of an inner shaft 44 of the driver. An outer sleeve line 46 may be provided on the outer sleeve 42, at a central region of the laser line window 40. As the outer sleeve 42 moves relative to the inner shaft 44, an inner shaft line 48 on the inner shaft 44 can align with the outer sleeve line 46, indicating to the user that the anchor 14 is inserted into the drilled hole (not shown). When the lines 46, 48 are aligned, the anchor 14 is 2 mm below the bone surface. If the surgeon wants to place the anchor flush with the bone surface the lines 46, 48 is at the far left side of the window 40. As the user threads the back handle 50 of the driver 20, the inner shaft line 48 will pull upwards (distally to proximally) in the direction of the user's hands while turning the anchor 14 to properly fit the anchor 14 into the drilled hole.

FIG. 9 shows a starting position (with the implant 12 removed for clarity). As can be seen, the anchor 14 is spaced apart from the end of the eyelet 16 and a front handle 52 of the driver 20 is adjacent the back handle 50 of the driver 20. Once the anchor 14 is positioned, as can be seen from FIGS. 10 and 11, the anchor 14 is adjacent the eyelet 16 (and, in some embodiments, the anchor 14 directly abuts the eyelet 16) and the front handle 52 of the driver 20 is spaced away from the front handle 50 of the driver 20.

Figure 12:
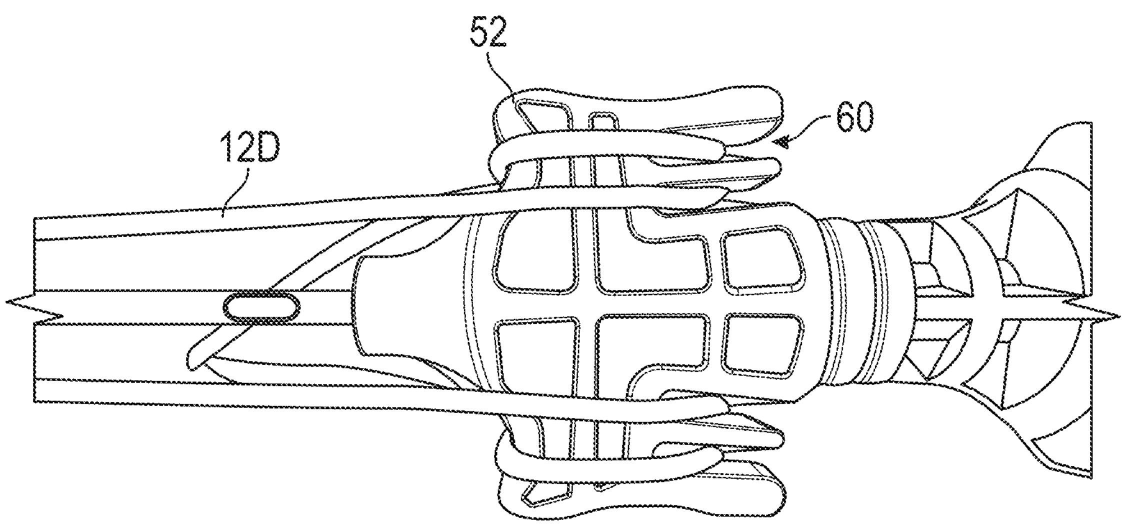
FIG. 12 illustrates a detailed view showing double looped cleat slots of the driver of the tissue reinforcement system of FIG. 1, shown with the tails of the implant secured thereto.

FIG. 12 illustrates double looped cleat slots 60 for the cords 12D (also referred to as the tails) of the implant 12 to be adequately secured to the front handle 52 of the driver 20. Typically, the implant 12 can be secured to the cleat slots 60 both during use and during the packaging/transportation of the system.

Figure 13:
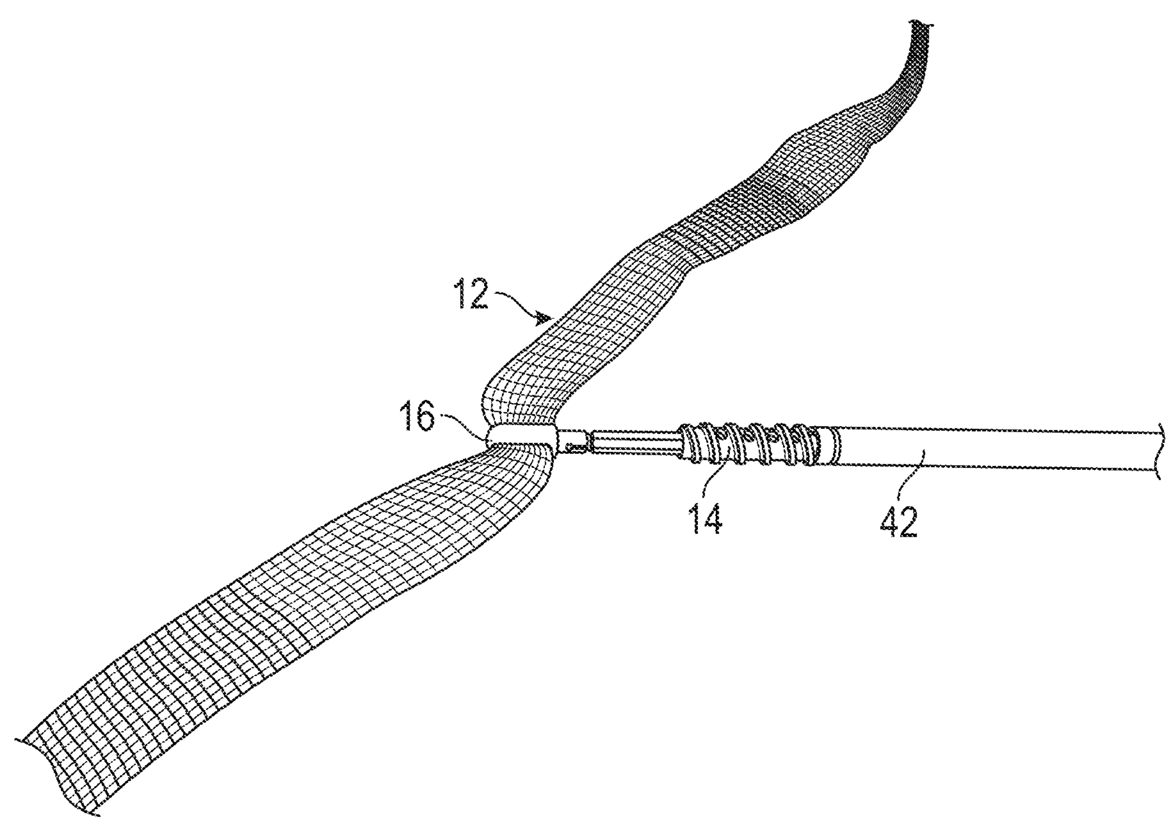
FIG. 13 illustrates a detailed perspective view of the eyelet of the tissue reinforcement system of FIG. 1, attached to the driver with the implant threaded thereon.

FIG. 13 illustrates how the eyelet 16 creates an interference fit on the tip of the driver 20 along with a preloaded anchor. The implant 12 is threaded/pulled through the eyelet 16 on the distal end of the driver 20.

Referring to the details of the above described Figures, the paragraphs below describe the general procedure steps for using the system 10 of the present invention. It should be understood that the below are exemplary steps and variations, reordering, removal or addition of steps may be contemplated within the scope of the present invention.

Example Process

Figure 14A:
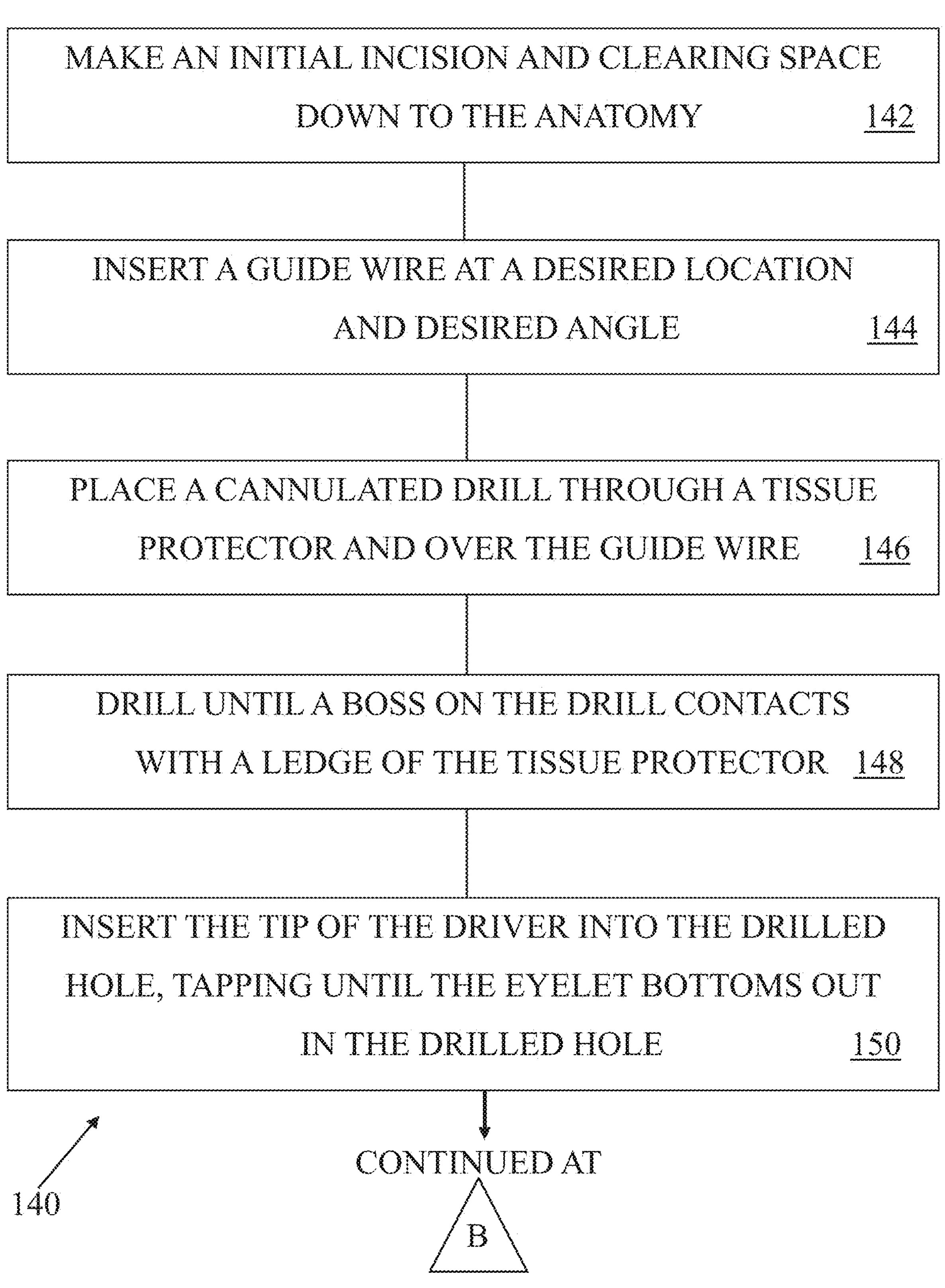
FIGS. 14A and 14B illustrate a method for augmenting and reinforcing soft tissue according to an exemplary embodiment of the present invention.
Figure 14B:
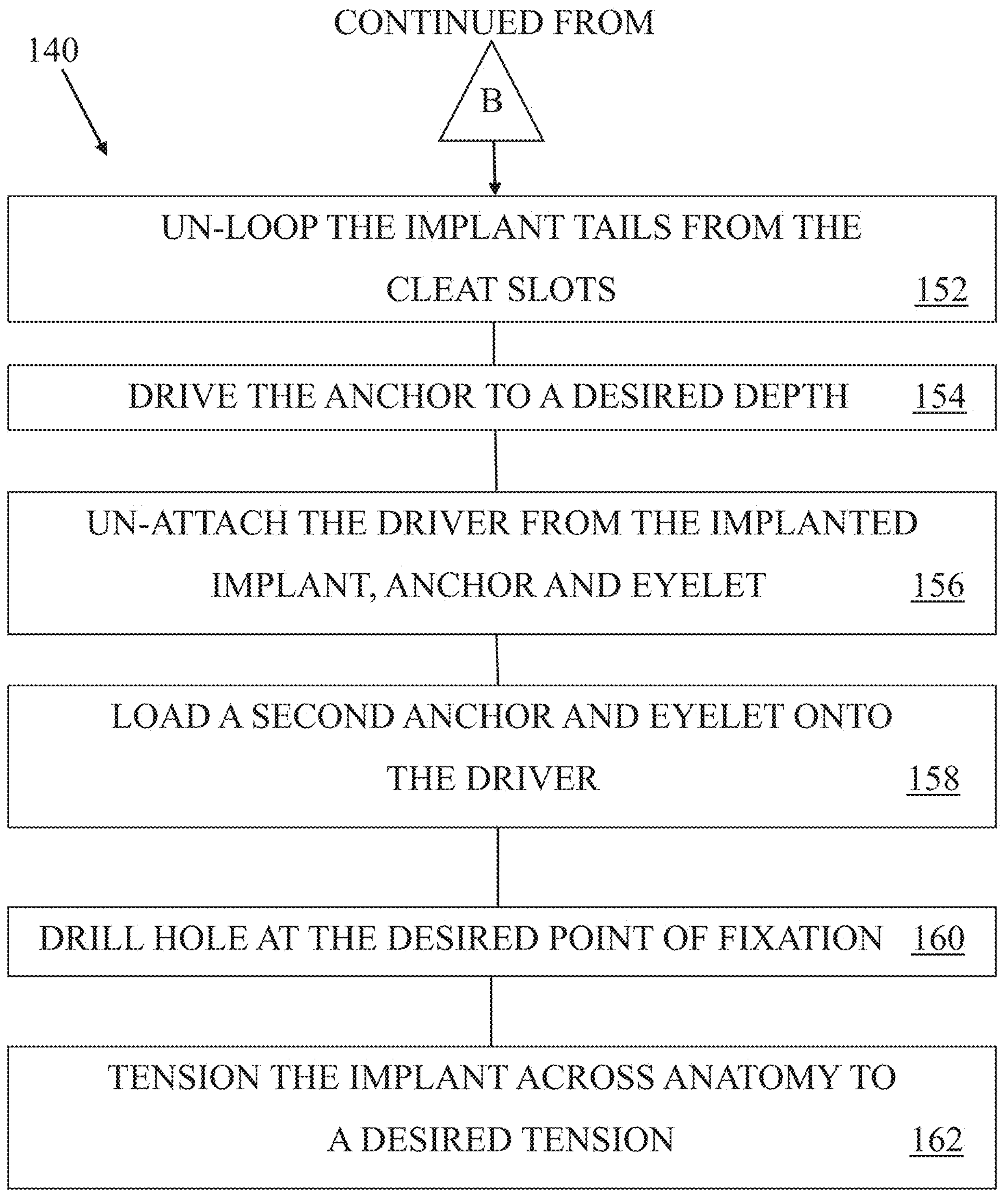

It may be helpful now to consider a high-level discussion of an example process. To that end, FIGS. 14A and 14B present an illustrative process related to the method for augmenting and/or reinforcing soft tissue. Process 140 is illustrated as a collection of blocks, in a logical flowchart, which represents a sequence of operations that can be implemented through the use of the components described above, for example. In the process, the order in which the operations are described is not intended to be construed as a limitation, and any number of the described blocks can be combined in any order and/or performed in parallel to implement the process.

Figure 15:
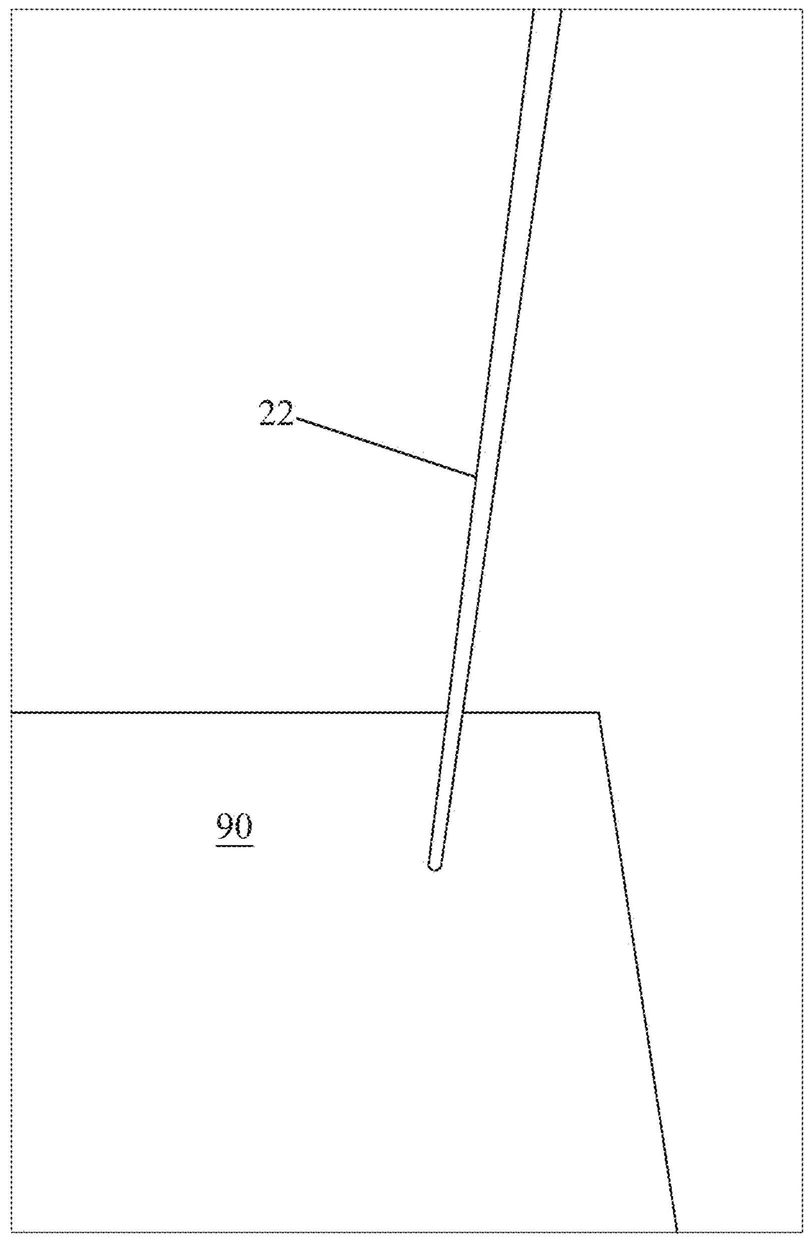
FIG. 15 shows an illustrative bone having a guide wire positioned thereon, according to an embodiment of the present invention.
Figure 16:
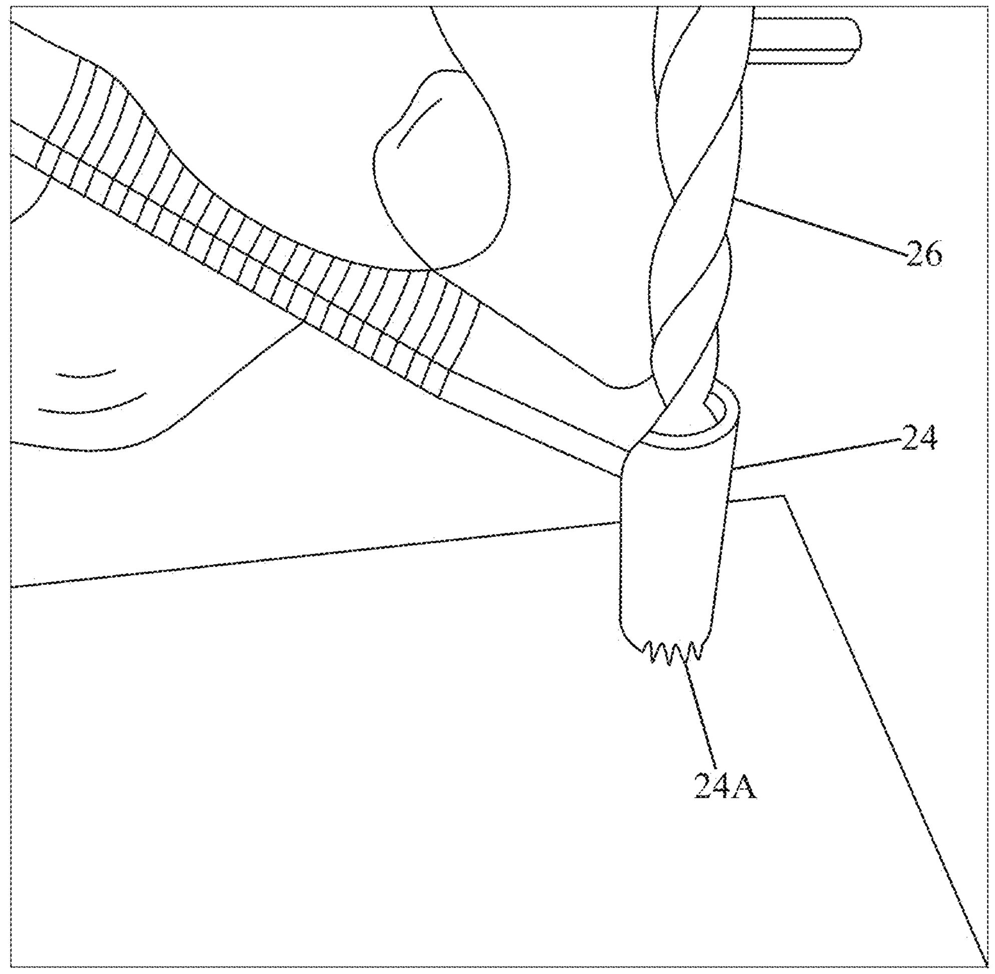
FIG. 16 illustrates positioning of the tissue protector and drill to form a hole in the bone, according to an embodiment of the present invention.

Referring now to FIGS. 14A and 14B, a process 140 for reinforcing and/or augmenting soft tissue can include a step 142 of making an initial incision and clearing space down to the anatomy, such as a bone surface 90. In step 144, a guide wire, such as one of the guide wires 22 (see FIG. 15), can be inserted at a desired location and angle. After attaching the canulated drill 26 to a power drill (not shown) and using the provided tissue protector 24, the cannulated drill 26 can be placed through the tissue protector 24 and over the guide wire 22 in step 146 (see FIG. 16).

The distal end of the tissue protector 24 has teeth 24A to ensure proper purchase and to avoid surrounding soft tissue windup and damage from the rotating drill . . . . In step 148, the user can drill until a boss 26A on the drill 26 contacts with a ledge of the tissue protector 24, as this indicates that the full depth needed for the anchor has been achieved in the bone.

Figure 17:
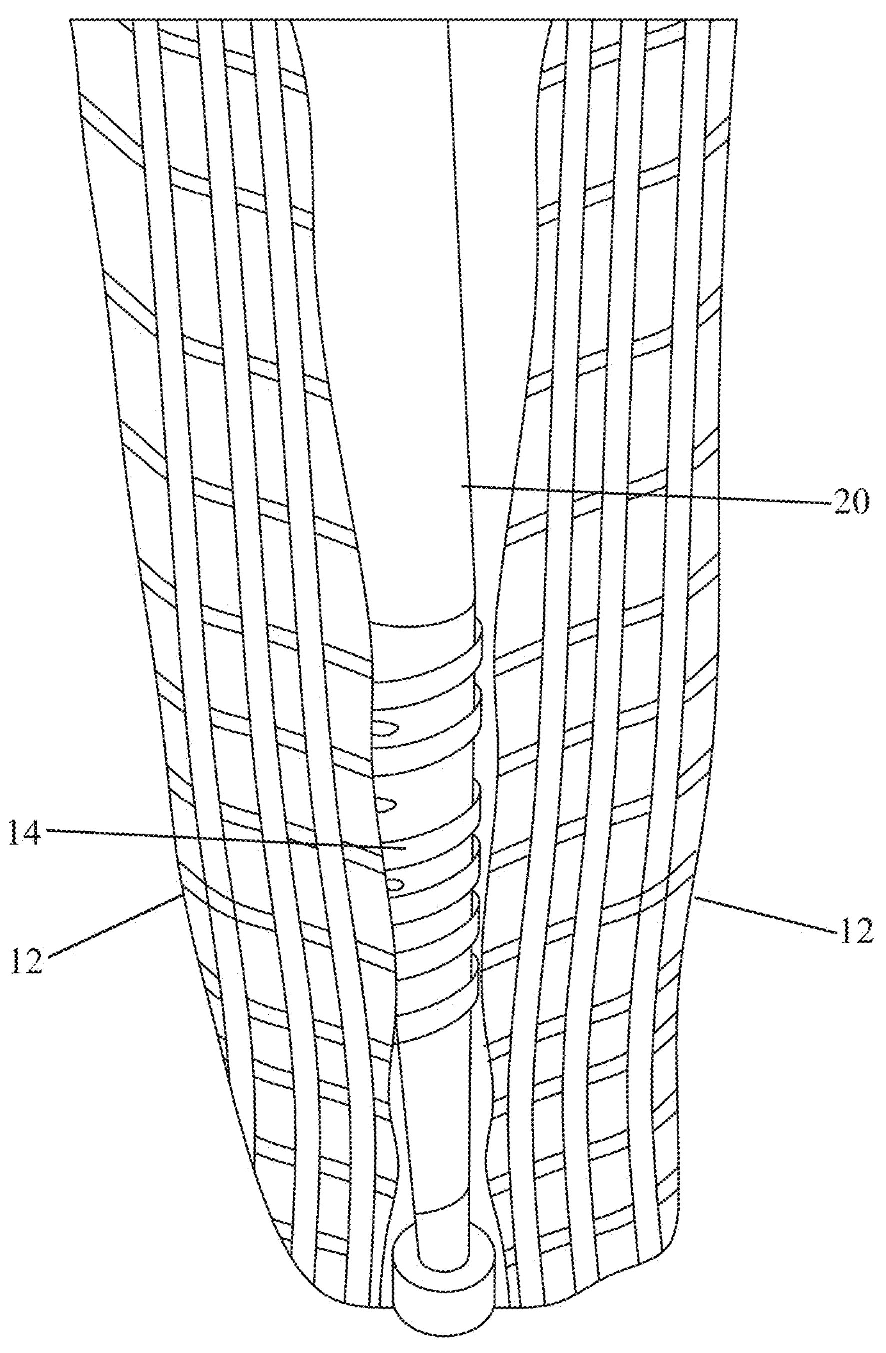
FIG. 17 illustrates positioning of the implant with the driver into the hole drilled by an action from FIG. 16, according to an embodiment of the present invention.

The driver 20, which is preloaded with a desire-sized anchor 14, eyelet 16 and the implant 12, can be removed from its package. In step 150, the tip of the driver 20 can be inserted into the hole (not shown) drilled on the previous step and the driver 20 can be tapped until the eyelet 16 bottoms out in the drilled hole (see FIG. 17). In some embodiments, use of a small mallet may be needed. In other embodiments, a tap 32 may be used to tap out the drilled hole to permit easier rotatable insertion of the anchor 14.

Figure 18:
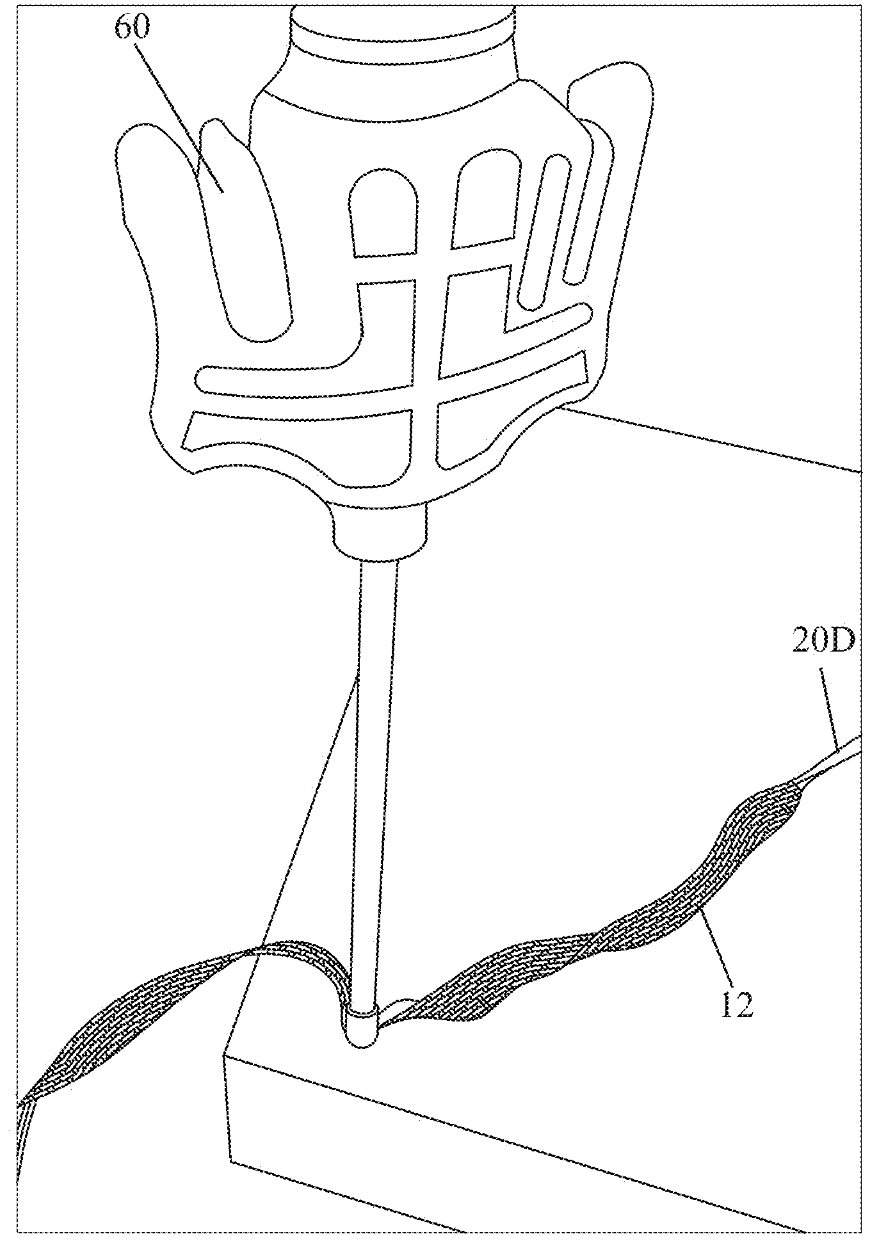
FIG. 18 illustrates the suture tails being unwrapped from the cleats in the handle of the drive, according to an embodiment of the present invention.
Figure 19:
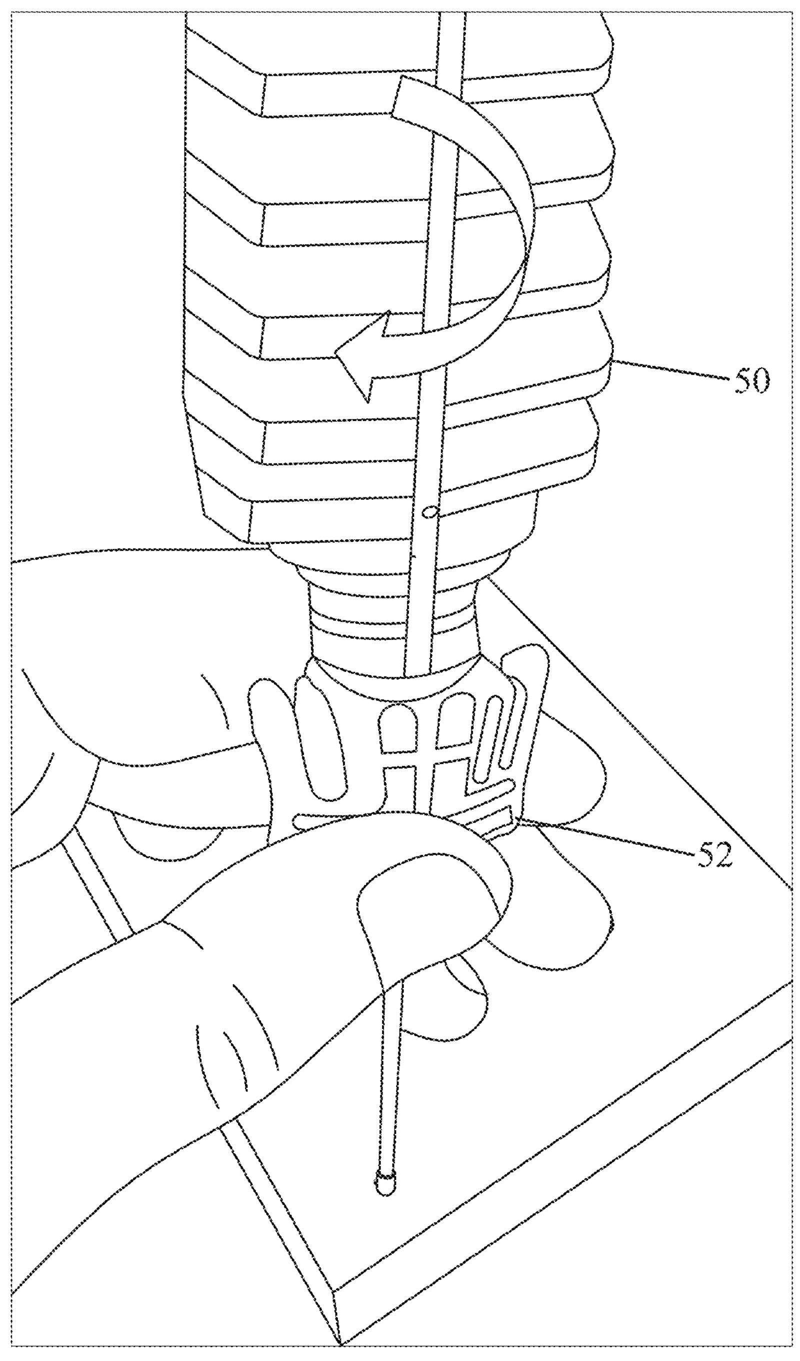
FIG. 19 illustrates rotation of the driver handle to place the anchor body and implant in the bone, according to an embodiment of the present invention.
Figure 20:
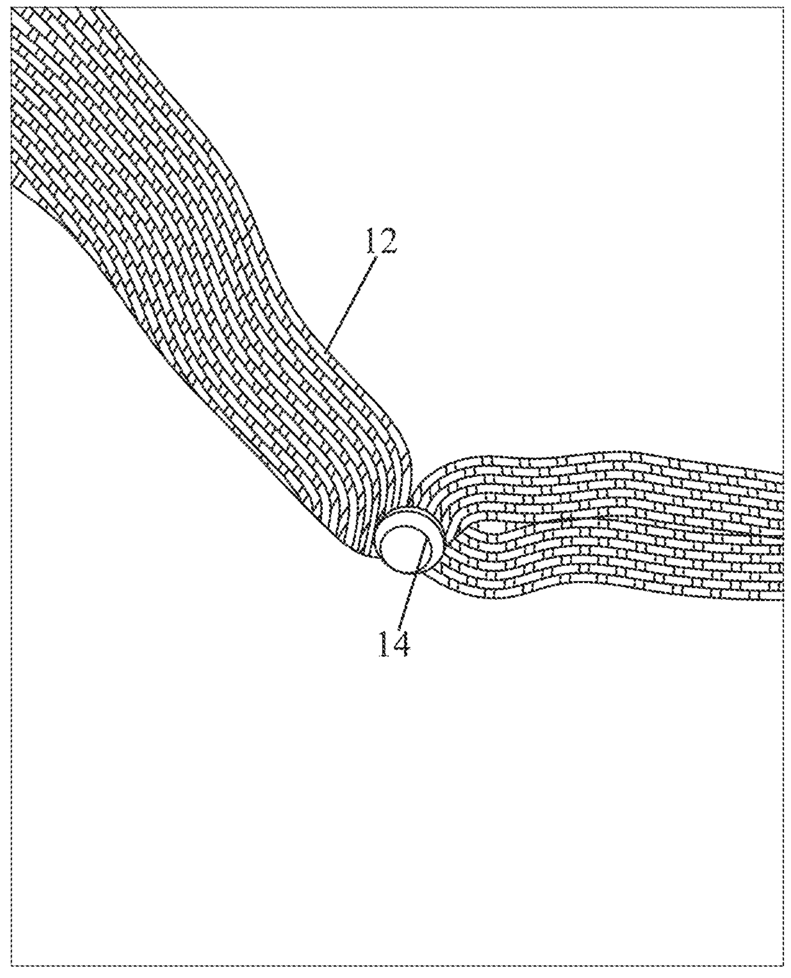
FIG. 20 illustrates removal of the driver, leaving behind the implant, secured with the anchor body within the drilled hole, according to an embodiment of the present invention.

In step 152 (see FIG. 18), the implant tails 20D can be un-looped from the cleat slots 60 and, in step 154 (see FIG. 19), the anchor 14 can begin being driven to a desired depth by holding the front handle 52 and the outer sleeve 46 of the driver 20 in a fixed position and twisting the back handle 50 of the driver 20 in a clockwise direction, ensuring visualization of the laser line window 40 under the cleat slots 60 of the front handle 52.

As the anchor 14 is driven into the bone, the inner shaft line 48 will begin to move closer to the user's hands within the laser line window 40 (distal to proximal in direction). Once the inner shaft line 48 is in line with the outer sleeve line 46, this indicates that the anchor 14 has been fully seated to a depth of roughly 2 mm sub-flush. In step 156 (see FIG. 19), the driver assembly can be gently pulled to un-attach the driver 20 from the implanted implant 12, anchor 14 and eyelet 16.

For the second point of fixation, in step 158, a second anchor 30 and eyelet 28 can be loaded onto the driver 20. The end of the implant 12 can be threaded through the eyelet 28. In step 160, a hole can be drilled at the desired point of fixation.

For proper tensioning across anatomy, in step 162, the implant 12, attached to the driver 20, can be pulled to the next drilled hole and at a desired tension. A marker or pen can be used to mark a line on the implant 12 up on the shaft where end of the anchor would be positioned. The center of the eyelet 28 can be aligned with the mark on the implant 12 and the above steps of driving the anchor 30 until the lines 46, 48 align can be repeated. This will ensure that the desired pre-determined tension is applied to the implant 12 across the desired anatomy.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A soft tissue augmentation device, comprising:

a driver having a shaft extending therefrom, the shaft including an outer sleeve, an inner shaft movable within an interior of the outer sleeve, and a window formed in the outer sleeve adjacent a handle of the driver, the handle being positioned at a proximate end of the shaft;

an eyelet removably positioned at a distal end of the shaft;

an anchor, rotatable by the driver, positioned on the shaft, adjacent the eyelet; and an implant configured to thread through the eyelet, the implant having ends operable to removably attach to the handle of the driver, wherein the anchor is movable between an initial position and a fully inserted position, wherein, at the fully inserted position, a single shaft marking disposed along the inner shaft is visible in the window and aligns with a single sleeve marking on the outer sleeve.

2. The soft tissue augmentation device of claim 1, wherein:

the second marking on the outer sleeve includes an outer sleeve line disposed on the outer sleeve at a central region of the window; and the first marking on the inner shaft includes an inner shaft line disposed on the inner shaft, wherein the anchor is movable between an initial position and a fully inserted position, wherein, at the fully inserted position, the inner shaft line is visible in the window and aligns with the outer sleeve line.

3. The soft tissue augmentation device of claim 1, wherein the handle includes a front handle and a back handle, the back handle rotatable relative to the front handle.

4. The soft tissue augmentation device of claim 3, further comprising double looped cleat slots operable to secure the ends of the implant thereto.

5. The soft tissue augmentation device of claim 1, further comprising:

a guide wire; and a cannulated drill, wherein:

the guide wire is configured to be positioned at a location and angle for drilling into bone; and the cannulated drill fits about the guide wire to position the drill at a proper position and angle for drilling into the bone.

6. The soft tissue augmentation device of claim 5, further comprising a tissue protector, wherein:

the drill passes through the tissue protector; and the drill includes a boss that contacts the tissue protector when the drill drills a hole at a predetermined desired depth.

7. The soft tissue augmentation device of claim 1, wherein the eyelet includes a slit with an increased diameter portion, the slit operable to receive an end of the shaft of the driver, the slit operable to permit removal of the eyelet from the shaft of the driver.

8. The soft tissue augmentation device of claim 1, wherein the anchor has a helical thread.

9. The soft tissue augmentation device of claim 1, wherein the anchor has a hex drive feature operable to engage with a hexagonal shaped end of the shaft of the driver.

10. The soft tissue augmentation device of claim 1, wherein the anchor includes one or more slots formed therein for increasing a surface area of the anchor.

11. The soft tissue augmentation device of claim 1, further comprising a tap, the tap configured to tap a hole for positioning the anchor therein.

12. The soft tissue augmentation device of claim 1, wherein the implant includes:

a tubular central portion of suture tape material having a pore size from 100 microns to 1 mm;

pockets formed on each end of a length of the central portion;

a second suture material portion at ends of the pockets; and a taper disposed at ends of the second suture material portion, the taper operable to reduce a width of the implant to form cords at each end of the implant.

13. A soft tissue augmentation device, comprising:

a driver having a shaft extending therefrom, the shaft including an outer sleeve, an inner shaft movable within an interior of the outer sleeve, and a window formed in the outer sleeve adjacent a handle of the driver, the handle being positioned at a proximate end of the shaft;

an eyelet removably positioned at the end of the shaft;

an implant operable to be threaded through an elongated opening of the eyelet, the implant having a flat width from 2 mm to 20 mm, the implant tapering down to terminate in circular cords for facilitating threading through the eyelet; and an anchor, rotatable by the driver, positioned on the shaft, adjacent the eyelet, the anchor having a helical thread, wherein:

the anchor is movable between an initial position and a fully inserted position, wherein, at the fully inserted position, a single shaft marking disposed along the inner shaft is visible in the window and aligns with a single sleeve marking on the outer sleeve; and the elongated opening having a length from 2 mm to 10 mm, the eyelet formed in a unitary construction, with a smooth and continuous exterior about the elongated opening, with the eyelet being free from moving parts.

14. The soft tissue augmentation device of claim 13, wherein the anchor includes:

a hex drive feature operable to engage with a hexagonal shaped end of the shaft of the driver; and one or more slots formed therein for increasing a surface area of the anchor.

15. The soft tissue augmentation device of claim 13, wherein the eyelet includes a slit with an increased diameter portion, the slit operable to receive an end of the shaft of the driver, the slit operable to permit removal of the eyelet from the shaft of the driver.

16. The soft tissue augmentation device of claim 13, wherein the implant includes:

a tubular central portion of suture tape material having a pore size from 100 microns to 1 mm; pockets formed on each end of a length of the central portion; and a second suture material portion at ends of the pockets.

17. A soft tissue augmentation device, comprising:

a driver having a shaft extending therefrom;

a handle connecting to the shaft;

an eyelet removably positioned at the end of the shaft; and an anchor, rotatable by the driver, positioned along the shaft, adjacent the eyelet, the anchor having a helical thread; wherein:

the eyelet includes a mounting end formed as a hollow tubular member, the mounting end having a first width;

the hollow tubular member having a single slit extending inward along the hollow tubular member, with an increased diameter portion at an internal end thereof;

the slit and the hollow tubular member operable to receive an end of the shaft of the driver;

the slit operable to permit removal of the eyelet from the shaft of the driver;

the anchor having an inside diameter larger than the first width of the mounting end of the eyelet to permit the mounting end to fit inside the anchor; and the eyelet having a lip at a distal end of the hollow tubular member, the lip increasing a diameter of the eyelet to a second diameter, the second diameter being greater than the inside diameter of the anchor to prevent the eyelet from moving through the anchor, the lip having a lip planar surface that abuts an anchor planar end surface of the anchor when the anchor is positioned on the shaft adjacent the eyelet.

18. The soft tissue augmentation device of claim 17, wherein the shaft of the driver includes:

an outer sleeve;

an inner shaft movable within an interior of the outer sleeve;

a window formed in the outer sleeve adjacent the handle;

an outer sleeve line disposed on the outer sleeve at a central region of the window; and an inner shaft line disposed on the inner shaft, wherein the anchor is movable between an initial position and a fully inserted position, wherein, at the fully inserted position, the inner shaft line is visible in the window and aligns with the outer sleeve line.

19. The soft tissue augmentation device of claim 17, wherein the implant includes:

a tubular central portion of suture tape material having a pore size from 100 microns to 1 mm;

pockets formed on each end of a length of the central portion;

a second suture material portion at ends of the pockets; and a taper disposed at ends of the second suture material portion, the taper operable to reduce a width of the implant to form cords at each end of the implant.

* * * * *